United States Patent [19]
Fairbanks et al.

[11] Patent Number: 6,054,461
[45] Date of Patent: Apr. 25, 2000

[54] TREATMENT OF NEUROPATHIC PAIN

[75] Inventors: Carolyn A. Fairbanks, NE. Rochester; George L. Wilcox, N. Golden Valley; Tinna M. Laughin, Anoka, all of Minn.

[73] Assignee: Solvay Pharmaceuticals GmbH, Hannover, Germany

[21] Appl. No.: 09/152,343

[22] Filed: Sep. 14, 1998

Related U.S. Application Data

[60] Provisional application No. 60/059,021, Sep. 16, 1997.

[51] Int. Cl.$^7$ .................................................. A61K 31/505
[52] U.S. Cl. .......................... 514/269; 514/256; 514/816; 514/818
[58] Field of Search ..................................... 514/256, 269, 514/816, 818

[56] References Cited

FOREIGN PATENT DOCUMENTS

9214453 A1   3/1992   WIPO .

OTHER PUBLICATIONS

Li et al., "Characterization of the Antinociceptive Properties of Cimetidine and a Structural Analog", *J. Pharmacology and Exp. Therapeutics* 276(2):500–08 (1996).
Ziegler et al., "Pharmacology of Moxonidine, a $I_1$–Imidazoline Receptor Agonist", *J. Cardiovascular Pharmacology* 27(Suppl. 3): S26–S37 (1996).
Laughlin et al., "Spinally Administered Dynorphin A Produces Long–Lasting Allodynia: Involvement of NMDA But Not Opioid Receptors", *Pain* 72:253–60 (1997).
M. Stanton–Hicks et al., "Reflex sympathetic dystrophy: changing concepts and taxonomy," *Pain*, 63 (1995), pp. 127–133.
K. D. Davis et al., "Topical application of clonidine relieves hyperalgesia in patients with sympathetically maintained pain," *Pain*, 47 (1991), pp. 309–317.
D. L. Tanelian, "Reflex Sympathetic Dystrophy, A Reevaluation of the Literature," *Pain Forum*, 1996, pp. 247–256.
Beitel, R.E. et al., "Response of Unmyelinated (C) Polymodal Nociceptors to Thermal Stimuli Applied to Monkey's Face," *Journal of Neurophysiology*, vol. 39, No. 6, Nov. 1976, pp. 1160–1175.
Johansson, R.S. et al., "Thresholds of Mechanosensitive Afferents in the Human Hand as Measured with Von Frey Hairs," *Brain Research*, vol. 184, (1980) pp. 343–351.
LaMotte, R.H. et al., "Tactile Detection of a Dot on a Smooth Surface: Peripheral Neural Events," *Journal of Neurophysiology*, vol. 56, No. 4, Oct. 1986, pp. 1109–1128.
Ossipov, M.H. et al., "Synergistic Antinociceptive Interactions of Morphine and Clonidine in Rats with Nerve–ligation Injury," *Anesthesiology*, vol. 86, No. 1, Jan. 1997, pp. 196–204.
Vanderah, T.W. et al., "Single intrathecal injections of dynorphin A or des–Tyr–dynorphins produce long–lasting allodynia in rats: blockade by MK–801 but not naloxone," *Pain*, vol. 68, (1996), pp. 275–281.

*Primary Examiner*—Dwayne C. Jones
*Assistant Examiner*—C. Delacroix-Muirheid
*Attorney, Agent, or Firm*—Evenson, McKeown, Edwards & Lenahan, P.L.L.C.

[57] ABSTRACT

A method of relieving neuropathic pain uses moxonidine and its physiologically compatible acid-addition salts for the treatment and/or prophylaxis of neuropathic pain. A composition comprising an effective amount of moxonidine, or a pharmaceutically acceptable salt thereof, in a pharmaceutically acceptable carrier, is administered to a subject in need of such treatment. The composition may be administered intrathecally.

4 Claims, 4 Drawing Sheets

TREATMENT OF NEUROPATHIC PAIN

This application relies on the priority of provisional application Ser. No. 60/059,021 (filed on Sep. 16, 1997).

FIELD OF THE INVENTION

The present invention relates to the treatment and/or prophylaxis of neuropathic pain.

BACKGROUND OF THE INVENTION

Neuropathic pain is a category of pain, which includes several forms of non-nociceptive chronic pain, which result from dysfunction of nervous rather than somatic tissue. The majority of non-nociceptive chronic pain, in terms of either syndromes or cases, follow at various times after damage to either central or peripheral nervous tissue. Diagnosis of most of these syndromes and cases reveals a dependence on abnormal spatial and temporal summation of natural somatic stimulation in the spinal cord and independence from somatic disease and peripheral sympathetic nervous system activity. The scientific pain research community defines this kind of pain as centrally mediated neuropathic pain and recognizes mechanistic, diagnostic, and therapeutic commonalties among pains of this class and differences between these and other syndromes. Neuropathic pain can be defined as pain deriving from damage to or inflammation of central or peripheral nervous systems. Examples of pain syndromes of this class include post herpetic neuralgia, neuritis, temporomandibular disorder, myofascial pain, back pain, pain induced by inflammatory conditions. Neuropathic pain may occur in all body regions. Thus, neuropathic pain may e.g. originate from dental region. Burn injury also often leads to neuropathic hyperalgesia in the affected body area. Neuralgia is characterized, in its acute phase, by intraneural inflammation which can cause damage to primary afferent axons, thus inducing neuropathic pain. Neuropathic pain may also be induced by diabetic conditions (diabetic neuropathy). Neuropathy of primary afferent axons in long nerves is found in diabetic patients. Nociceptor sensitization may ensue.

Neuropathic pain conditions are characterized by hyperesthesia (enhanced sensitivity to a natural stimulus), hyperalgesia (abnormal sensitivity to pain), allodynia (widespread tenderness, characterized by hypersensitivity to tactile stimuli), and/or spontaneous burning pain. In humans, neuropathic pain tends to be chronic. Neuropathic pain is generally considered to be non-responsive or only partially responsive to conventional opioid analgesic regiments. Consequently, alternate therapies for the management of this form of chronic or neuropathic pain are widely sought.

It is an object of the invention to provide compounds with neuropathic pain alleviating activity and to develop new pharmaceutical preparations suitable for the treatment and/or prophylaxis of neuropathic pain, having a favourable therapeutic ratio with only low side effects.

SUMMARY OF THE INVENTION

The invention pertains to a method of relieving neuropathic pain. More specificly the present invention concerns the use of 4-chloro-5-[(4,5-dihydro-1H-imidazol-2-yl)-amino]-6-methoxy-2-methylpyrimidine (generic name: moxonidine) and its physiologically compatible acid-addition salts for the treatment and/or prophylaxis of neuropathic pain. In accordance with the method, a composition comprising an effective amount of moxonidine, or a pharmaceutically acceptable salt thereof, in a pharmaceutically acceptable carrier, is administered to a subject in need of such treatment. In one embodiment of the invention the moxonidine is administered intrathecally.

These and other objects and features of the invention will become more fully apparent when the following detailed description of the invention is read in conjunction with the accompanying examples.

DETAILED DESCRIPTION OF THE INVENTION

Figure 1:
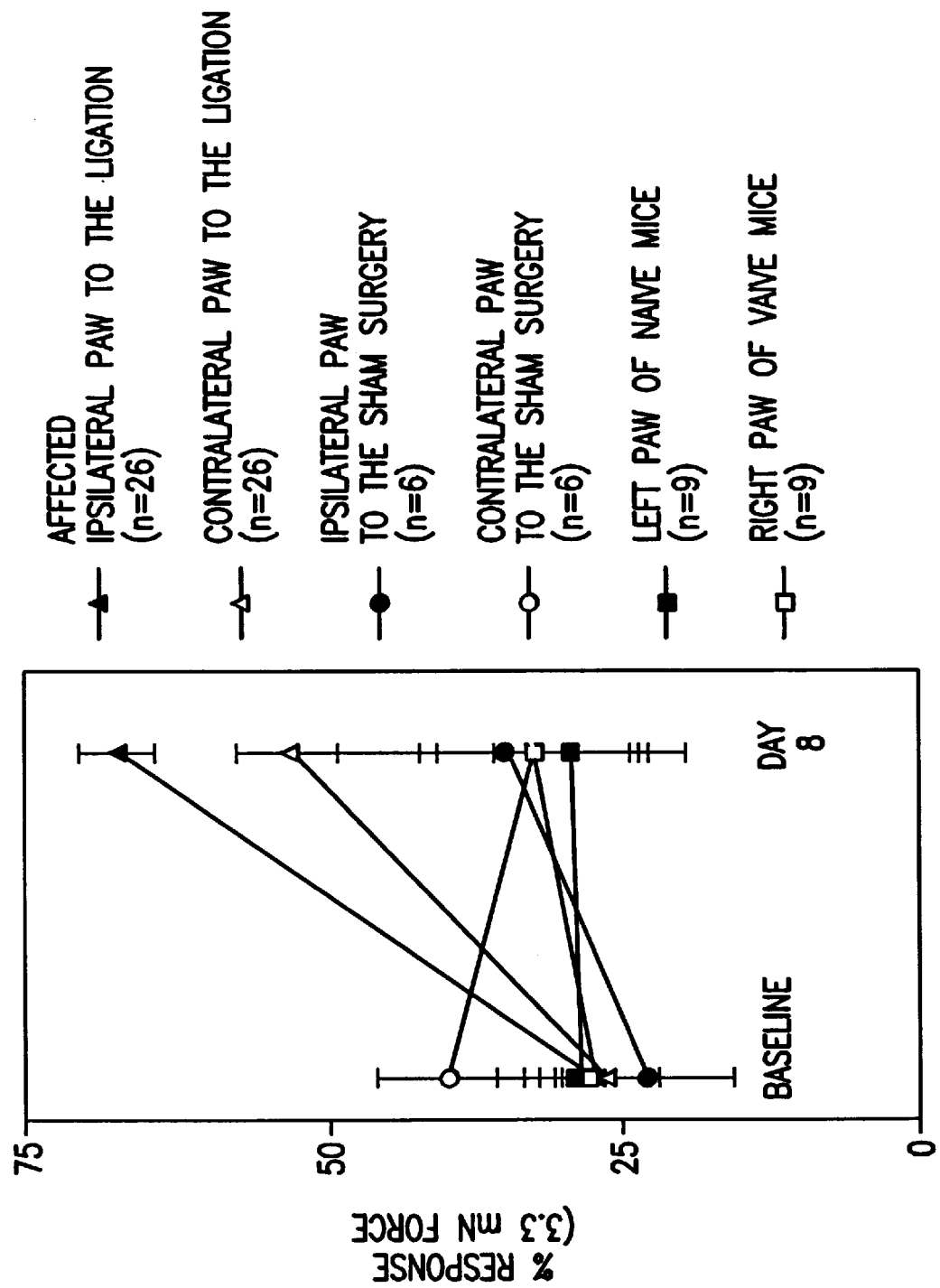
FIG. 1 shows responsivity curves (% response to mechanical stimulation) which were generated in mice after induction of allodynia by L5 spinal nerve ligation.

According to the invention, 4-chloro-5-[(4,5-dihydro-1H-imidazol-2-yl)-amino]-6-methoxy-2-methylpyrimidine (generic name: moxonidine) of formula I

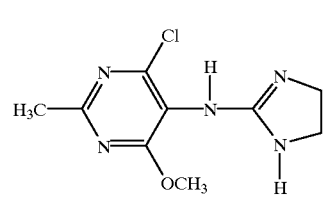

and its physiologically compatible acid-addition salts are used for the manufacture of pharmaceutical preparations for the treatment and/or prophylaxis of neuropathic pain.

Salts with inorganic acids, such as hydrohalic acids, or with organic acids, for example lower aliphatic monocarboxylic or dicarboxylic acids such as acetic acid, fumaric acid or tartaric acid or aromatic carboxylic acids such as salicylic acid are suitable as physiologically compatible acid-addition salts of moxonidine.

The compounds used in accordance with the invention are within the scope of the 5-[(2-imidazolin-2-yl)-amino]-pyrimidine derivatives with blood pressure lowering properties described in the published German Patent Application No. 28 49 537, and are known from this patent application. Pharmaceutical preparations containing moxonidine are commercially available as antihypertensive medications under the trade name Physiotens®. The compounds can be manufactured in a known manner essentially in accordance with the processes described in the aforementioned published German Patent Application or in a manner similar to these processes.

It has surprisingly been found that moxonidine and its physiologically compatible acid-addition salts have neuropathic pain alleviating action in larger mammals, in particular in humans, and are suitable for the treatment and/or prophylaxis of neuropathic pain. Nociceptor sensitization and its progression may be treated with moxonidine.

Generally, for treating neuropathic pain moxonidine may be administered according to known pharmaceutical methods. In many cases it will be advisable to treat the pain in a manner that addresses its specific source.

The neuropathic pain alleviating activity of moxonidine can be demonstrated in mice by standard tests for the evaluation of neuropathic pain inhibiting activities.

It has been found that in mice with dynorphin-induced allodynia or spinal nerve ligation-induced allodynia, two rodent models of neuropathic pain, the administration of moxonidine effectively alleviates allodynic hypersensitivity to mechanical stimuli or point pressure. This is a clear indication of the anti-allodynic activity of moxonidine. The experimental data found show that moxonidine is effective in relieving allodynia which is a form of neuropathic pain.

Thus, the results of the experiments according to the present invention demonstrate the potential for moxonidine for the treatment of neuropathic pain.

TEST AND RESULTS

List of Abbreviations:

AR: adrenergic receptors; $ED_{50}$ value: effective dose 50%; $ED_{80}$ value: effective dose 80%; $ID_{50}$: inhibitory dose 50% value; $I_1$: imidazoline$_1$; i.p.: intraperitoneal; i.t.: intrathecal; % MPE: percent maximum possible effect; µg: microgram; ng: nanogram; mg: milligram; mN: millinewton; nmol: nanomoles; pmol: picomoles; SP: substance P; S.D.: standard deviation; S.E.M.: standard error of the mean; vF filament: von Frey filament; x: arithmetic mean; #: number of behaviors.

Animals:

Experimental subjects were 15–30 g male ICR mice (Harlan, Madison, Wis.). Subjects were housed in groups of five to ten in a temperature- and humidity-controlled area and were maintained on a 12 hr light/dark cycle and had free access to food and water.

Chemicals:

Moxonidine hydrochloride (available from Solvay Pharmaceuticals GmbH, Hannover, Germany) was dissolved in an aqueous 1% by vol. acetic acid solution and diluted with acidified saline solution (pH 3.2–4). Dynorphin (from NIDA) was dissolved in an aqueous 0.9% by wt. saline solution. Both drugs were administered intrathecally (i.t.) by direct lumbar puncture to conscious mice.

Induction of Allodynia by L5 Spinal Nerve Ligation:

Allodynia can be induced in mice or in rats by surgical ligation of the L5 spinal nerve. Animals undergoing this procedure demonstrate increased sensitivity to application of otherwise normally innocous von Frey monofilaments. This L5 spinal nerve ligation was used to induce allodynia to investigate the ability of moxonidine to alleviate chronic pain. Groups of mice tested included:

Naive: required to determine the animals' baseline response (n=9);

Sham-operated: required as a control for changes induced by the surgery (n=6);

L5-ligated: required to induce nerve injury (n=34).

Mice were anesthetized with halothane. The left paraspinal muscle was separated from the spinous processes at the L4–S2 levels and removed. Removal of this muscle did not impair mobility of the animal following surgery. The L6 transverse process was then removed to identify visually the L4–L6 spinal nerves. The L5 spinal nerve was tightly tied (ligated) with 6-0 silk thread. After hemostasis was confirmed, the wounds were sutured with 3-0 silk thread and the skin closed with sterile wound clips. Animals recover mobility within 30 minutes. As a control, in a separate group of animals, a sham surgery identical to the above was performed. The only difference with the sham operated animals was that their nerves were not ligated.

Allodynia Testing in L5 Spinal Nerve Ligation Model:

Tactile Sensitivity:

Nociception was evaluated by responsiveness to multiple applications (10 per hind paw) of a single von Frey (vF) filament to the plantar surface of each hind paw. When the stimulus is of sufficient force, the mouse will withdraw and/or shake the paw; this action represents the behavioral endpoint. In nerve-injured mice, a vF filament (#3.61) exerting 3.3 mN of force elicited 70% responsivness on the paw ipsilateral to the injury. This level of stimulation is sufficient to test compounds for dose-dependent inhibition of the response to mechanical sensation.

Inhibition of Tactile Sensitivity:

Varying doses of moxonidine were administered to test for inhibition of the tactile sensitivity. Percent inhibition was determined relative to the mean number of hind paw withdrawals (elicited as described above) according to the following equation:

$$\% \text{ Inhibition} = \frac{(\# \text{ Paw Withdrawals BEFORE Drug} - \# \text{ of Paw Withdrawals AFTER Drug})}{\# \text{ Paw Withdrawals BEFORE Drug Treatment}}$$

Each mouse served as its own control and was used only once. The ED50 value and confidence limits were calculated according to the method of Tallarida and Murray.

Induction of Allodynia by Intrathecal Injection of Dynorphin:

Allodynia may be induced by a single intrathecal injection of 3 nmol dynorphin A (entire peptide). Administration of dynorphin results in an increase in mechanical sensitivity to innocous mechanical stimunlation of the hind paws, e.g., with von Frey filaments, that lasts for more than 70 days. Use of von Frey filaments to measure sensitivity to mechanical stimuli or point pressure is a well-established technique in pain research. Animals treated with dynorphin respond to von Frey filaments of low pressure that do not induce responses in normal (naive) animals. This hyperresponsivity indicates an increased sensitivity to stimuli that are normally not innocous. This test is a recognised standard test for evaluating allodynia and represents an animal model of central neuropathic pain.

Therefore, the dynorphin-induced allodynia model was used as a second chronic neuropathic pain model to investigate the ability of moxonidine to alleviate chronic pain. Groups of mice tested included:

Dynorphin/Saline-treated: required to confirm that the dynorphin effectively induced mechanical allodynia.

Dynorphin/Moxonidine-treated: testing the ability of moxonidine to inhibit the mechanical allodynia.

Allodynia Testing in Dynorphin-Induced Allodynia Model:

Tactile Sensitivity:

Nociception was evaluated by responsiveness to multiple applications (3 per hind paw) of a single von Frey filament to the dorsal surface of each hind paw. Because dynorphin injection does not selectively injure one side or the other of the spinal cord, the data gathered from each separate hind paw are pooled, representing a total of 6 stimulations per mouse. When the stimulus is of sufficient force, the mouse will withdraw and/or shake the paw; this action represents the behavioral endpoint. In dynorphin-treated mice, a vF filament (#2.44) exerting 0.4 mN of force elicited 50–60% responsiveness on the hind paws. This level of stimulation was sufficient to test compounds for dose-dependent inhibition of the response to mechanical sensation.

Inhibition of Tactile Sensitivity:

Moxonidine was administered to test for inhibition of the allodynia induced by dynorphin injection. Data are represented as percent response.

$$\% \text{ Response} = \frac{(\# \text{ of Paw Withdrawals Observed})}{6 \text{ stimulations}}$$

Statistical Analysis:

Data describing alleviation of neuropathic pain are expressed as means of percent maximal possible effect (% MPE) or percent inhibition (% inhibition) with standard error of the mean (S.E.M.). In experiments where full dose-response curves were generated, a minimum of three doses were used for each drug or combination of drugs. Potency differences are presented as dose ratios between the $ED_{50}$ values (the dose calculated to produce 50% MPE) of different dose-response curves. Statistical comparisons of potencies are based on the confidence limits of the $ED_{50}$ values. A shift in a dose-response curve is considered significant when the calculated $ED_{50}$ value of one curve falls outside the confidence limits of the $ED_{50}$ value of the curve to which it is being compared. The $ED_{50}$ values and confidence limits were calculated according to the method of Tallarida and Murray. In some experiments the statistical significance was evaluated using Student's t test (significance set at p<0.05). Groups of 6 or greater animals were used for each dose.

Figure 2:
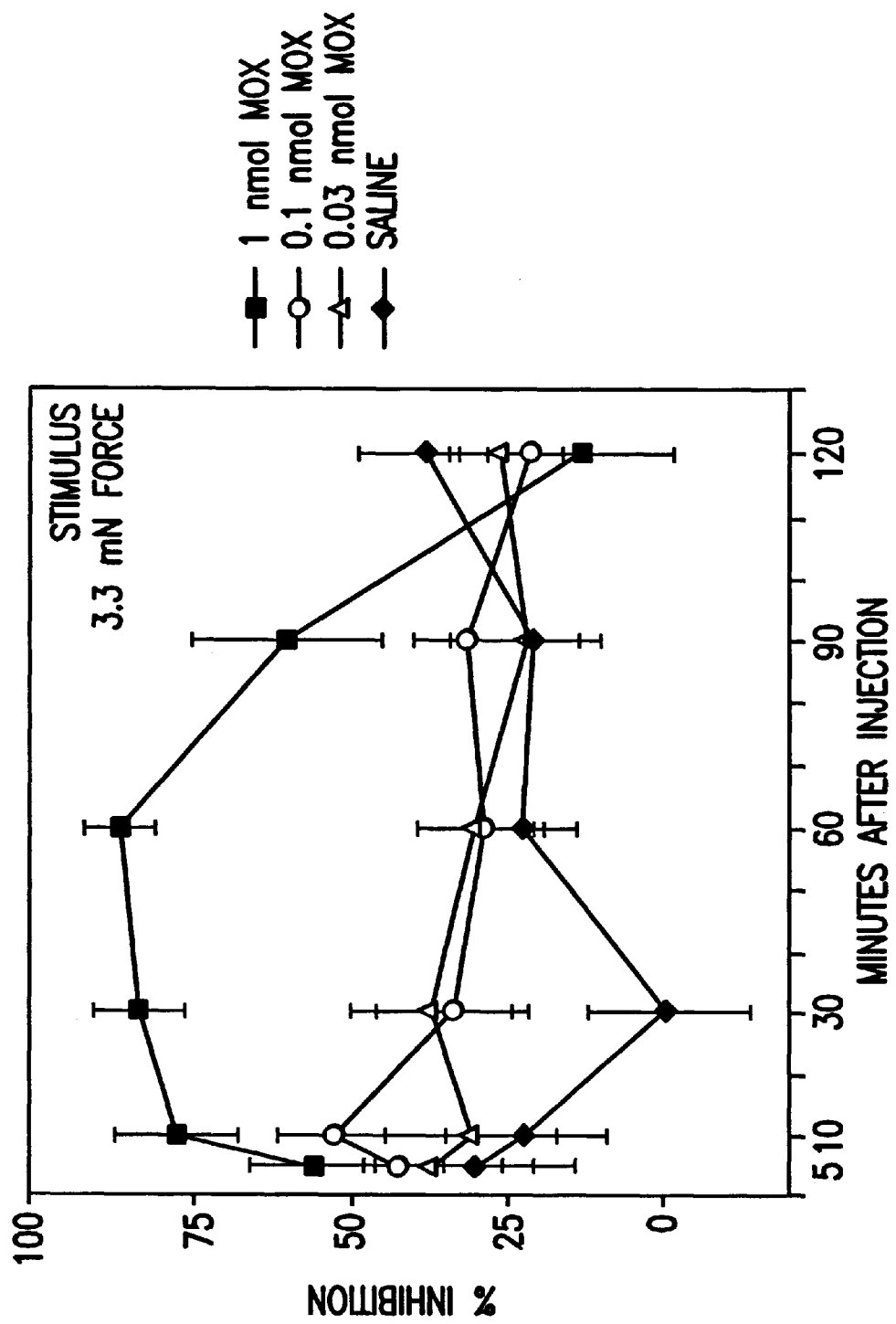
FIG. 2 shows time-dependent inhibition-response curves for moxonidine-induced inhibition of mechanical allodynia (induced by L5 spinal nerve ligation) in mice.
Figure 3:
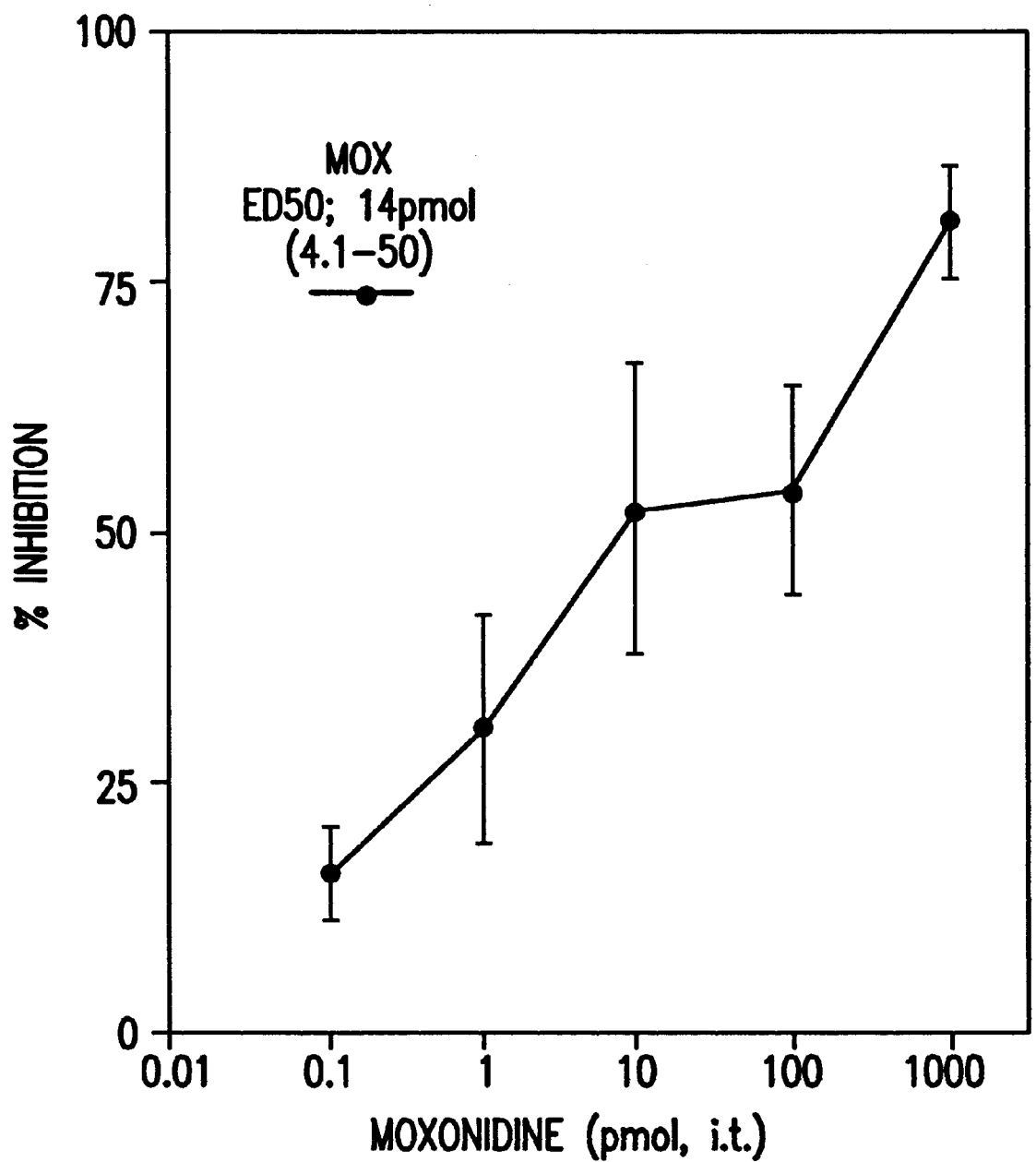
FIG. 3 shows a dose-dependent inhibition-response curve for moxonidine-induced inhibition of mechanical allodynia (induced by L5 spinal nerve ligation) in mice.
Figure 4:
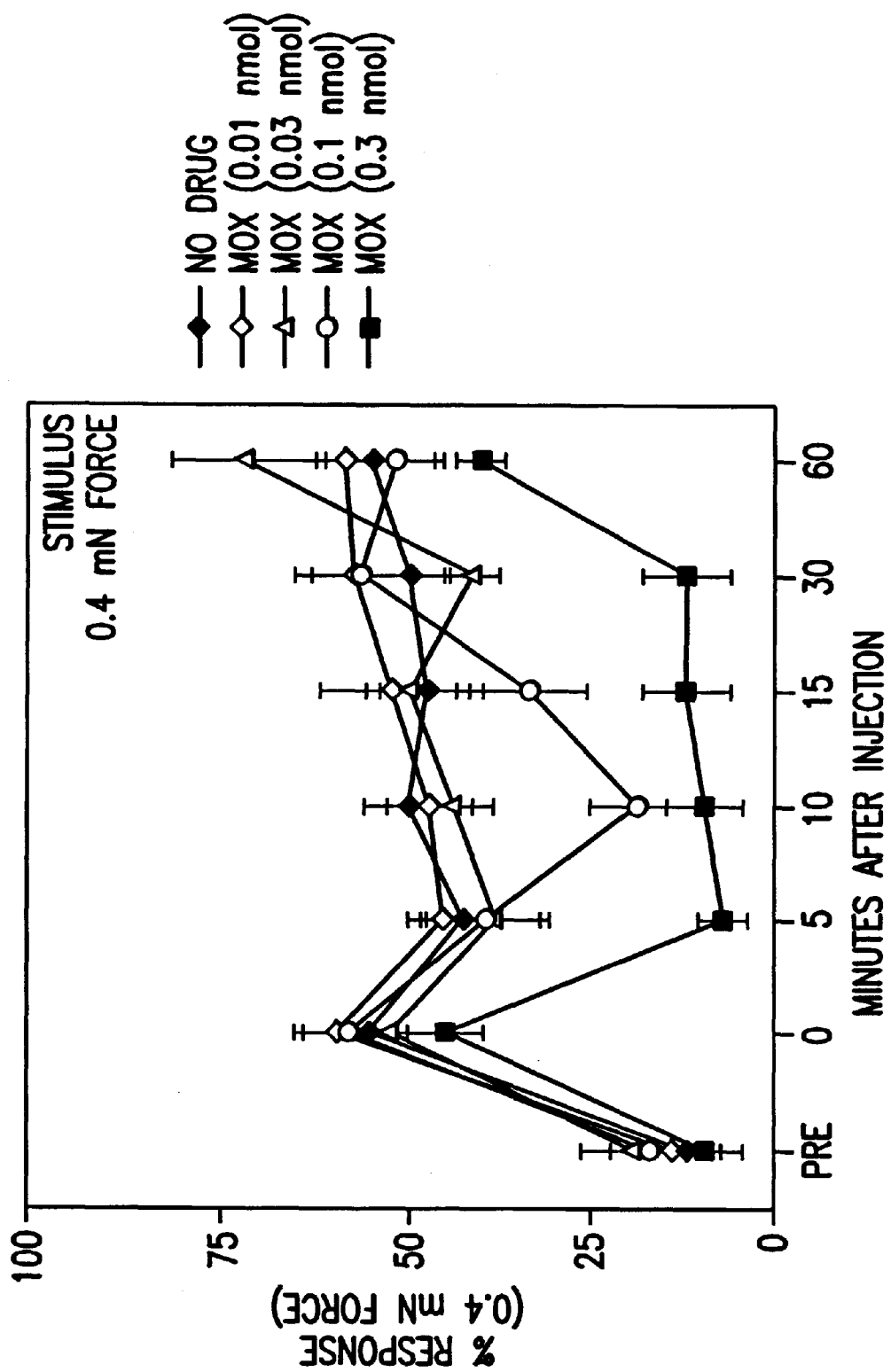
FIG. 4 shows time-dependent inhibition-response curves for moxonidine-induced inhibition of mechanical allodynia (dynorphin-induced) in mice.

FIG. 1 shows post-surgery responsivity curves (% response) to mechanical stimulation of the hind paws of mice with von Frey filaments on day 8 after induction of allodynia by L5 spinal nerve ligation. FIG. 2 and FIG. 3 show time-depending (FIG. 2) and dose-depending (FIG. 3) inhibition-response curves for moxonidine-induced inhibition of mechanical allodynia (induced by L5 spinal nerve ligation) after mechanical stimulation of the affected hind paw ipsilateral to the injury (affected) in mice. FIG. 4 shows time-depending inhibition-response curve for moxonidine-induced inhibition of mechanical allodynia (dynorphin-induced) after mechanical stimulation of the hind paws of mice.

INDUCTION OF ALLODYNIA DUE TO NERVE INJURY (L5 SPINAL NERVE LIGATION).

As shown if FIG. 1, no difference was observed in baseline % response to a force of 3.3 mN (vF filament #3.61, our calibration) between the left (x=23%, S.E.M.: 4.1%, n=34, closed triangles) and right hind paws (x=19%, S.E.M.: 3.3%, n=34, open diamonds) (p>0.05, Student's unpaired t test) of mice before injury. On day 8 post-surgery a substantial increase in responsivity was observed for both hind paws. The increase was significantly greater for the left hind paw (ipsilateral to the ligation, x=66%, S.E.M.: 2.9%, closed triangles) than for the right hind paw (contrala-teral to the ligation: x=51%, S.E.M.: 3.8%, open diamonds) (p<0.01, Student's unpaired t test). Both of these responses are substantially greater than either hind paw of the control animals. These animals include those mice that received sham surgery (left hind paw: x=35%, S.E.M.: 15%, n=6, closed circles; right hind paw, x=33%, S.E.M.: 8.4%, n=6, open circles) and naive mice (left hind paw: x=30%, S.E.M: 6.2%, n=9, closed squares; right hind paw mice: x=33%, S.E.M.: 9.9%, n=9, open squares). These differences demonstrate that the L5 spinal nerve ligation surgery is sufficient to produce allodynia in the hind paw ipsilateral to the injury.

MOXONIDINE-INDUCED DOSE-DEPENDENT ATTENUATION OF L5 SPINAL NERVE LIGATION-INDUCED ALLODYNIA.

The mechanical allodynia induced by tight ligation of the L5 spinal nerve in mice was measured with a 3.3 mN von Frey filament inhibition and expressed as the % response frequency in FIG. 1.

In a first test, moxonidine-induced inhibition of mechanical allodynia was measured. The results are represented in FIG. 2 and expressed as % inhibition of the % response (inhibition-response curve) to mechanical stimulation. Moxonidine at 1 nmol (filled squares) and 0.1 nmol (open circles) doses significantly attenuated the allodynia induced by dynorphin for 90 and 10 minutes, respectively, whereas 0.03 nmol (open triangles) moxonidine had minimal effect on allodynia. Intrathecal administration of saline (closed diamonds) had minimal effect on L5 ligation-induced allodynia. The mean±S.E.M. represents the percent inhibition. (n=7–8 animals/dose).

A second test for measuring the moxonidine-induced dose-dependent inhibition of L5 ligation-induced allodynia was conducted. The anti-allodynic effect was measured only at the 10 minute time. The data were expressed as a inhibition-response curve and represented in FIG. 3. Five doses of moxonidine were administered (0.1, 1, 10, 100, 1000 pmol, i.t. n=5–7 mice per dose). Moxonidine inhibited paw withdrawals with an ED50 value of 14 pmol (4.1–50).

MOXONIDINE DOSE-DEPENDENT ATTENUATION OF DYNORPHIN-INDUCED ALLODYNIA.

The mechanical allodynia induced by a single intrathecal injection of dynorphin A (enire peptide) was measured with a von Frey filament (#2.44) that exerts 0.4 mN of force. The data are expressed as the % response frequency and represented in FIG. 4. Moxonidine at 0.3 nmol (filled squares) and 0.1 nmol (open circles) doses significantly attenuated the allodynia induced by dynorphin for 30 and 15 minutes, respectively; while 0.03 nmol (open triangles) and 0.01 nmol (open diamonds) moxonidine had no effect on allodynia. Administration of intrathecal saline (closed diamonds) had no effect on dynorphin-induced allodynia. The mean±S.E.M. represents the percent response frequency of foot withdrawals to 6 trials (n=6 animals/dose).

The foregoing test results show that moxonidine and its acid-addition salts exert a neuropathic pain alleviating activity. Moxonidine and its acid-addition salts are therefore suitable as medicaments for the treatment and/or prophylaxis of neuropathic pain in larger mammals, especially in humans, and in particular for the treatment and/or prohylaxis of severe chronic neuropathic pain. Moxonidine may be given by all known administration routes. The doses to be administered may differ between individuals and naturally vary depending on the type of condition to be treated and the route of administration. For example, locally applicable formulations, in particular intrathecally injectable formulations, generally contain substantially less amount of active substance than systemically applicable formulations. For example solutions containing 10 to 100 $\mu$g per single unit dosage form are suitable for intrathectal injections. Continous application may be needed for chronic neuropathic pain conditions.

According to a preferred embodiment of the present invention moxonidine is administered intrathecally. Intrathecal administration allows local application of the compound to those regions of the spinal cord, such as to dorsal horn regions at affected vertebral levels, where polysynaptic relay of pain sensation occurs. Intrathecal administration, either as a bolus dosage or as a constant infusion, delivers the compound directly to the subarachnoid space containing cerebral spinal fluid (CSF). The main advantage of this route of administration is that effective pain release can be achieved by i.t. applied doses that are considerably lower than systemically applied doses.

For administration according to the invention the active quantities of the compounds that alleviate neuropathic pain can be contained together with customary pharmaceutical excipients and/or additives in solid or liquid pharmaceutical formulations.

Examples of solid dosage forms are such as solid, semisolid, lyophilized powder, tablets, coated tablets, pills, capsules, powders, granules or suppositories, also in form of sustained release formulations. These solid dosage forms can contain standard pharmaceutical inorganic and/or organic excipients. Such excipients include pharmaceutical grades of mannitol, lactose, starch, magnesium stearate, sodium saccharine, talcum, cellulose, glucose, gelatine, sucrose, magnesium carbonate, and the like in addition to customary pharmaceutical additives such as fillers, lubricants or tablet disintegrants. Liquid preparations such as solutions, suspensions or emulsions of the active ingredients can contain the usual diluents such as water, oil and/or suspending aids such as polyethylene glycols and such like. Further additives such as preservatives, flavouring agents and such like may also be added.

The active ingredients can be mixed and formulated with the pharmaceutical excipients and/or additives in a known manner. For the manufacture of solid dosage forms, for example, the active ingredients may be mixed with the excipients and/or additives and granulated in a wet or dry process. Granules or powder can be filled directly into capsules or compressed into tablet cores. If desired, these can be coated in the known manner.

Liquid preparations can be prepared by dissolving or dispersing the compounds and optional pharmaceutical adjuvants, in a carrier, such as, for example, aqueous saline, aqueous dextrose, glycerol, or ethanol, to form a solution or suspension.

The following example is intended as a more detailed illustration of the manufacture of pharmaceutical preparation containing moxonidine that are suitable for the treatment and/or prophylaxis of neuropathic pain, without, however, limiting the scope of the application.

EXAMPLE

A liquid preparation containing moxonidine for intrathecal administration is composed of:
Moxonidine hydrochloride: 15 mg
Isotonic aqueous saline solution: quantum satis ad 1 l
Moxonidine was dissolved in the saline solution. The resulting solution was filled into ampouls of 1 ml content and sterilised.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of treatment and/or prophylaxis of centrally mediated neuropathic pain in a mammal, comprising administering to the mammal a composition comprising:
   an effective neuropathic pain relieving amount of the compound of formula I,

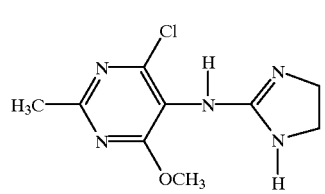

or a pharmaceutically acceptable acid-addition salt thereof, and
   at least one of a pharmaceutical excipient or an additive.

2. The method according to claim 1, wherein said composition is administered intrathecally.

3. A method of treatment and/or prophylaxis of neuropathic pain in a mammal, comprising administering to the mammal a composition comprising:
   an effective neuropathic pain relieving amount of the compound of formula I,

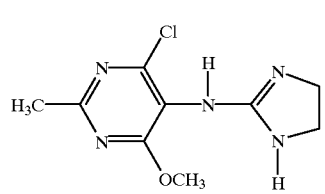

or a pharmaceutically acceptable acid-addition salt thereof; and
   at least one of a pharmaceutical excipient or an additive,
   wherein said neuropathic pain is a neuropathic pain induced by a diabetic condition.

4. The method according to claim 3, wherein said composition is administered intrathecally.

* * * * *